United States Patent
Herzhaft et al.

(10) Patent No.: US 6,769,295 B2
(45) Date of Patent: Aug. 3, 2004

(54) CONTINUOUS MEASUREMENT OF THE RHEOLOGICAL CHARACTERISTICS OF WELL FLUIDS

(75) Inventors: Benjamin Herzhaft, Suresnes (FR); Lionel Rousseau, Issou (FR); Bernard Duperray, Ars (FR); Laurent Perier, Lyons (FR)

(73) Assignee: Institut Francais du Petrole, Malmaison Cedex (FR)

( * ) Notice: Subject to any disclaimer, the term of this patent is extended or adjusted under 35 U.S.C. 154(b) by 0 days.

(21) Appl. No.: 10/268,720

(22) Filed: Oct. 11, 2002

(65) Prior Publication Data

US 2003/0084717 A1 May 8, 2003

(30) Foreign Application Priority Data

Oct. 19, 2001 (FR) .................................. 01/13

(51) Int. Cl.⁷ ............................ G04F 1/00; E21B 47/12; G01F 1/68
(52) U.S. Cl. .................... 73/152.19; 73/54.27; 166/295
(58) Field of Search .......................... 073/152.19, 54.27, 073/575

(56) References Cited

U.S. PATENT DOCUMENTS

| | | | |
|---|---|---|---|
| 2,607,217 A | | 8/1952 | Merten et al. |
| 2,774,239 A | * | 12/1956 | Fitzgerald .................... 73/575 |
| 3,777,551 A | | 12/1973 | Weiss |
| 4,327,587 A | | 5/1982 | Docekal et al. |
| 4,643,020 A | * | 2/1987 | Heinz ........................ 73/54.27 |
| 4,915,708 A | * | 4/1990 | Prevedello et al. ........... 44/280 |
| 5,042,296 A | * | 8/1991 | Burgess .................... 73/152.19 |

(List continued on next page.)

FOREIGN PATENT DOCUMENTS

| | | |
|---|---|---|
| FR | 2588664 | 4/1987 |
| WO | 0102832 | 2/2001 |

OTHER PUBLICATIONS

"Bingham Plastic Model", date unknown, http://www.glossary.oilfield.sib.com, Schlumberger.*

The Influence of Molecular Weight and Thermal History on the Thermal, Rheological, and Mechanical Properties of Metallocene–Catalyzed Linear Polyethylenes, Jordens et al, X0004200054 vol. 41, o. 19, Sep. 2000.

Viscoelasticity of Biodegradable Polymer Blends of Poly(3–hydroxybutyrate) and Poly(ethyl n oxide), Park et al vol. 42,No. 13, Jun. 2001 XP004232651.

Rhe –Mechanical and Rhe –Opt cal Characterisation of Ultra High Molecular Mass P ly(m thylmethacrylat ) in Solution, vol. 42, No. 6, Mar. 2001 Dell 'Erba t al XP004223290.

Primary Examiner—Hezron Williams
Assistant Examiner—Rose M. Miller
(74) Attorney, Agent, or Firm—Antonelli, Terry, Stout & Kraus, LLP

(57) ABSTRACT

The present invention relates to a method and to a system for monitoring the evolution of the characteristics of a fluid circulating in a well (1) for example, wherein complex dynamic viscosity measurements are performed with a suitable detector (6) arranged on a line (5) through which said fluid circulates, so as to obtain a law of variation of the complex dynamic viscosity $\eta^*$ as a function of $2\pi f$; a rheogram of the fluid, i.e. a law of variation of the viscosity $\eta$ as a function of the shear ($\dot{\gamma}$), is deduced therefrom; Va, Vp and YV are calculated from the rheogram; these stages are repeated after a predetermined time interval; the evolution of the characteristics of the fluid is deduced from these measurements.

6 Claims, 1 Drawing Sheet

U.S. PATENT DOCUMENTS

| | | | | |
|---|---|---|---|---|
| 5,327,984 A | * | 7/1994 | Rasi et al. | 175/61 |
| 5,470,900 A | * | 11/1995 | Sasaki et al. | 524/269 |
| 5,612,294 A | * | 3/1997 | Vaussard et al. | 507/110 |
| 5,777,212 A | | 7/1998 | Sekiguchi et al. | |
| 6,065,539 A | * | 5/2000 | Noik et al. | 166/295 |
| 6,562,905 B1 | * | 5/2003 | Nummila-Pakarinen et al. | 525/191 |
| 6,625,566 B1 | * | 9/2003 | Peysson et al. | 702/706 |

* cited by examiner

CONTINUOUS MEASUREMENT OF THE RHEOLOGICAL CHARACTERISTICS OF WELL FLUIDS

FIELD OF THE INVENTION

The present invention relates to a method of determining the rheological characteristics of well drilling fluids according to API (American Petroleum Institute) standards. What is understood to be rheological characteristics is: the rheological curve (or law of variation of the viscosity $\eta$ as a function of the shear ($\dot{\gamma}$)), the apparent viscosity Va, the plastic viscosity Vp and the yield value YV. The invention allows continuous measurement of these values by means of a device arranged on the mud-return line.

BACKGROUND OF THE INVENTION

Measurement of the rheological characteristics of well fluids is part of the conventional measurements performed on a drilling site. These measurements, standardized by the API, are not performed on a continuous basis on the mud-return line, but on fluid samples taken in this line or in tanks. Well fluids are characterized in a more or less regular way according to operations. These measurements are carried out, in the best case, by means of a two-speed or six-speed FANN 35 type device. This device is equipped with coaxial cylinders. It determines a shear stress as a function of the shear rate. Other measurements, much more precise but however sporadic, are sometimes performed in the laboratory by means of more sophisticated rotating rheometers.

The object of the present invention is to allow automation of this rheology measurement in order to obtain continuous recording of the characteristics of a drilling fluid. It is thereby expected to obtain more reliable measurements than those currently performed by means of the FANN 35 on fluid samples which are not really representative of the circulating fluid. Monitoring of the drilling operation can be increased and will thus facilitate quasi-immediate detection of anomalies occurring during this operation (water inflow, well fluid degradation, sedimentation, . . . ). This in-line measurement allows to anticipate these technical problems more rapidly. It therefore prevents a disastrous economic impact on the progress of the drilling operation.

In-line rotating rheometers were tested on drilling sites, but they appeared to be inadequate because of the fragility of the rotating parts.

SUMMARY OF THE INVENTION

The present invention thus relates to a method for monitoring the evolution of the characteristics of a circulating fluid, for example in a well. According to the invention, the following stages are carried out:

carrying out complex dynamic viscosity measurements with a suitable detector arranged on a line through which said fluid circulates, so as to obtain a law of variation of the complex dynamic viscosity $\eta^*$ as a function of $2\pi f$, where f is the excitation frequency of the detector, deducing therefrom the rheogram of the fluid, i.e. a law of variation of the viscosity $\eta$ as a function of the shear ($\dot{\gamma}$), calculating at least one characteristic parameter of the rheology of the fluid from said rheogram, repeating these stages after a predetermined time interval, deducing from the evolution of said parameter the evolution of the characteristics of the fluid.

According to the method, the rheogram can be deduced by means of a calibration function depending on the type of detector and on the nature of the fluid.

The calibration function can be obtained from measurements on the initial fluid prior to circulating it.

The measurements can include measurements performed with said detector suited to obtain the complex dynamic viscosity and measurements performed with a FANN type rotating viscometer.

A new calibration function can be calculated upon each fluid change.

Va, Vp and YV can be calculated by means of said rheogram.

Said viscosity variation laws can be modeled according to one of the following models: Ostwald (power law), Hershell-Bulkley, Casson.

The invention also relates to a system for monitoring the evolution of the characteristics of a fluid circulating in a well for example, comprising:

a detector arranged on a line through which said fluid circulates, suited to measure the complex dynamic viscosity, calculation means for implementing the above method, means for recording the evolution of the fluid characteristics.

BRIEF DESCRIPTION OF THE DRAWINGS

Other features and advantages of the present invention will be clear from reading the description hereafter of a non-limitative example, with reference to the accompanying drawings wherein.

DETAILED DESCRIPTION

Figure 1:
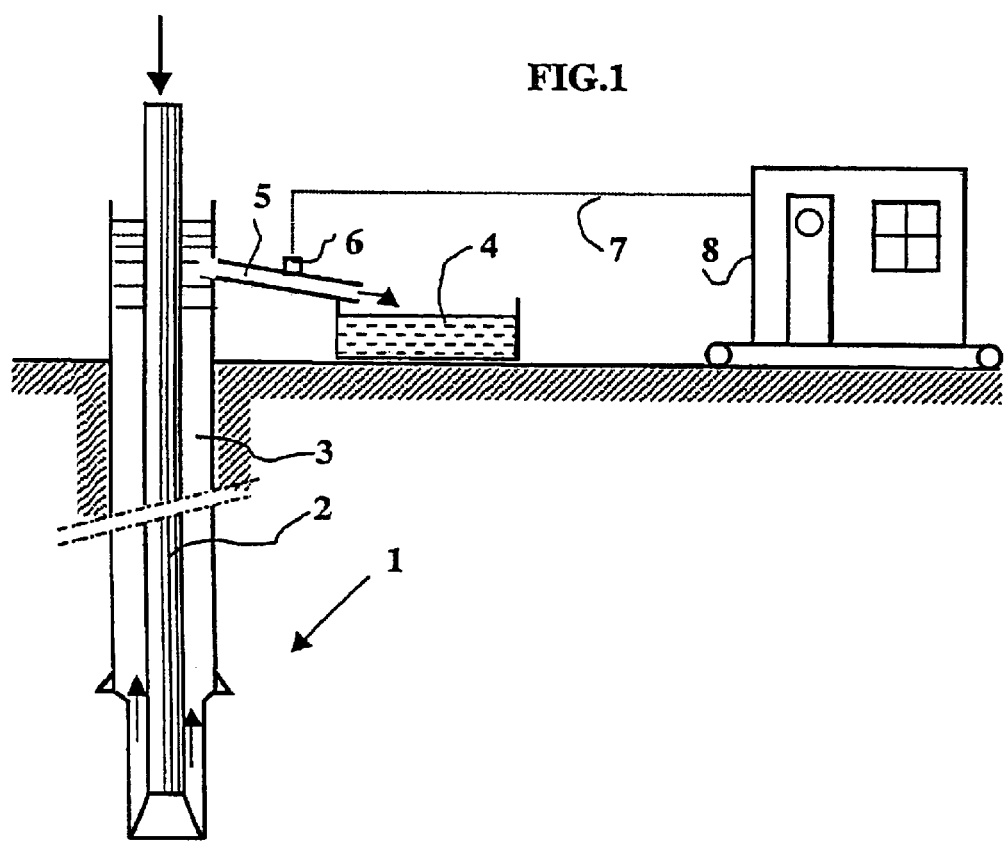
FIG. 1 diagrammatically shows the system according to the invention.

FIG. 1 diagrammatically shows a well drilling installation 1 wherein, according to the art, the drilling fluid is injected into drill string 2, flows up to the surface through annulus 3, then through a line 5 into the fluid processing installation diagrammatically represented by tank 4. A specific measuring device 6 gives a measurement in connection with the rheology of the fluid flowing through flowline 5. This measurement is transmitted through a cable 7 to a control and measuring cab 8. This cab can be a mud logging cab, i.e. intended for logging during drilling so as to monitor the progress of the drilling operation. According to the invention, the rheology of the return fluid is measured on a continuous or practically continuous basis so as to monitor the rheological evolution of the drilling fluid.

Detector 6 can be the detector developed by the METRAVIB R.D.S. company and known as VISCOPROCESS. It can work in-line and the measurements are performed on a continuous basis. It therefore allows a more automated control of the well fluids and of the drilling operation in general. It is more robust than certain in-line rotating rheometers owing to its technical design because it is designed without any moving parts, hence a limited maintenance. The VISCOPROCESS detector is provided with a slot forming an air gap of some millimeters, for example between 1 and 3 mm, for two piezoelectric bimetallic strips arranged opposite each other. The first bimetal forms a transmitter connected to means intended to subject it to a harmonic stress in a frequency range (f) between 1 and 300 Hz so as to subject it to a flexural vibration at low deformations. The second bimetal arranged opposite the first one forms the receiver connected to means suited to detect the response of the well fluid present in the air gap to the vibration of the first bimetal. This response is transmitted to the electronic processing means.

The electronic processing unit associated with the detector allows:

to gain access, in a certain frequency range and at low deformations, to the viscous G" and elastic G' moduli of the well fluid considered, to thus gain access to the real part $\eta'$ and to the imaginary part $\eta''$ of the complex dynamic viscosity $\eta^*$ of the well fluids such that $\eta'=G''/2\pi f$, $\eta''=G'/2\pi f$ and $|\eta^*|=(\eta'^2+\eta''^2)^{0.5}$, to gain access to an equivalence between the shear viscosity measured under steady flow conditions and the complex dynamic viscosity $\eta^*$ by applying Cox-Merz's law such that $\eta(\dot\gamma)=|\eta^*|(\gamma_m 2\pi f)$, where $\gamma_m$ is the maximum deformation applied.

The present invention consists in applying these different laws to a method and to a system which allow continuous rheological characterization of well fluids.

This method first consists in characterizing the initial well fluid (i.e. the new and clean fluid) prior to any injection:

by means of a FANN 35, $\eta_{FANN}$ is determined as a function of $\dot\gamma(\eta_{FANN}=\tau_{FANN}/\dot\gamma)$ for a series of measurements according to the rotating speed of the FANN 35, then the curve $\eta_{FANN}=g(\dot\gamma)$ obtained is modeled by a power law determined by linear regression such that: $\eta_{FANN}=K_1 \cdot \dot\gamma^{n1-1}$, i.e. $\tau_{FANN}=K_1 \cdot \dot\gamma^{n1}$.

The $\eta^*$ values of the initial well fluid, prior to any injection, are then measured as a function of frequency f, for example by means of the VISCOPROCESS device. The curve $|\eta^*|=h(\gamma_m 2\pi f)$ thus obtained is modeled by means of a power law determined by linear regression such that: $|\eta^*|=K_2 \cdot (\gamma_m 2\pi f)^{n2-1}$, i.e. $\tau^*=K_2 \cdot (\gamma_m 2\pi f)^{n2}$.

The invention is not limited to the rheological model of the fluid, the power model (Ostwald), Hershell-Bulkley, Casson or others can be used:

Hershell-Bulkley: $\tau=\tau_0+K\dot\gamma^n$

Casson: $\sqrt{\tau}=\sqrt{\tau_0}+\sqrt{\eta_p \cdot \dot\gamma}$

Figure 2:
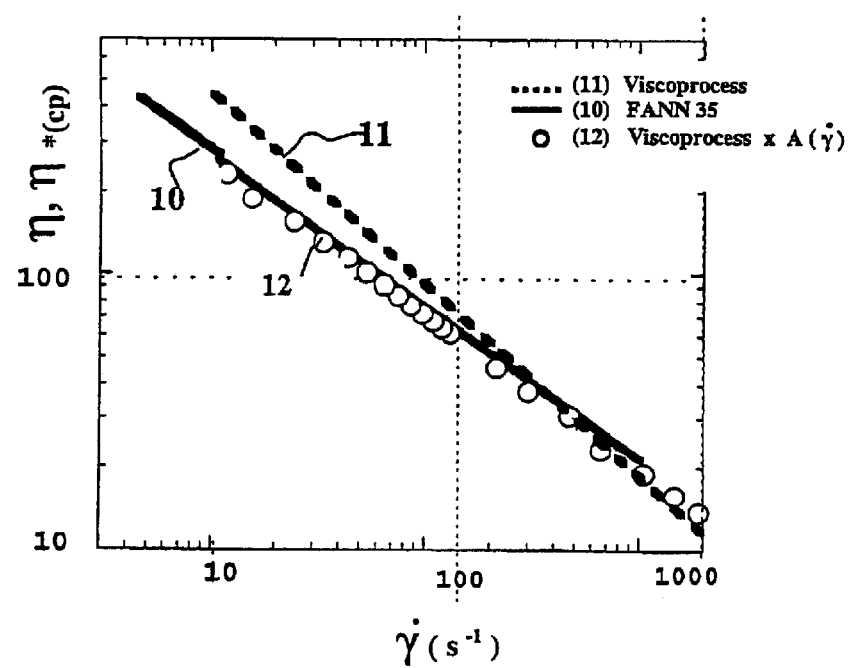
FIG. 2 shows a rheogram obtained according to the invention.

FIG. 2 shows curves 10 and 11 corresponding respectively to functions $\eta_{FANN}$ and $|\eta^*|$, in Log—Log unit, where $\dot\gamma$ and $(\gamma_m 2\pi f)$ are considered to be equivalent and on the abscissa.

A calibration function A is determined from these laws (curves 10 and 11) so that the two curves merge, i.e. $\eta_{FANN}=|\eta^*| \cdot A(\dot\gamma)$. The calibration result is illustrated by points 12. These measurements were obtained from a water-base drilling fluid having the composition as follows:

| | |
|---|---|
| IDVIS (xanthan) | 4 g/l |
| POLYLOSE (starch) | 12 g/l |
| PAM (polyacrylamide) | 3 g/l |
| GLYDRILL MC (glycol) | 5% by weight |
| NaCl | 200 g/l |
| NaOH | for pH = 9.5. |

During circulation of the drilling fluid in the well:

this calibration function is taken into account in the mathematical processing of the data acquired by the measuring device and received by the processing unit in the following form: $A(\gamma_m 2\pi f)=(K1/K2) \cdot (\gamma_m 2\pi f)^{n1-n2}$ where $\gamma_m$ is set at 1, the rheological characteristics of the well fluid are monitored throughout the drilling operation by means of the function $|\eta^*|(\gamma_m 2\pi f) \cdot A(\gamma_m 2\pi f)$ obtained from the measurement of G' and G" continuously delivered by the measuring device, the apparent viscosity Va in centipoise (cp) can be calculated from the rheological function obtained $Va=|\eta^*|(1020) \cdot A(1020)$, 1020 in $s^{-1}$ representing the shear gradient obtained by a FANN 35 at 600 rpm, the plastic viscosity Vp in centipoise (cp) can be calculated as $Vp=[1020 \cdot |\eta^*|(1020) \cdot A(1020)-510 \cdot |\eta^*|(510) \cdot A(510)]/510$, 5010 in $s^-$representing the shear gradient obtained by a FANN 35 at 300 rpm, the yield value YV in pounds/square feet (lbs/100 ft$^2$) can be calculated as $YV=2(Va-Vp)$.

The present invention thus affords the advantage of allowing continuous measurement of the rheological characteristics of the well fluid back from the bottomhole. Monitoring of these characteristics allows to follow the evolution of the nature of the well fluid during drilling, and events occurring during operations, such as fluid incidents, losses, external pollution, lithology change, inflow, etc., can be deduced through the complementary agency of other continuous measurements.

To sum up, this method consists in:

measuring throughout the drilling operation $|\eta^*|(\gamma_m 2\pi f) \cdot A(\gamma_m 2\pi f)$ equivalent to function $\eta(\dot\gamma)$, rheological characteristic of the mud ($\dot\gamma$ and $\gamma_m 2\pi f$ being considered to be equivalent). This function can be advantageously used for pressure drop, bottomhole pressure calculations;

continuously giving values of Va, Vp and YV similar to those which would be measured by means of the FANN 35 by the overseer in charge of checking the fluid.

The overseer in charge of monitoring the drilling fluid can rapidly visualize an evolution of the conventional parameters: Va, Vp, YV, which enables him to adjust the fluid by adding products, additives or base, thereto.

What is claimed is:

1. A method of monitoring the evolution of characteristics of a fluid circulating in a well for example, characterized in that the following stages are carried out:

obtaining a calibration function depending on the type of detector and nature of the fluid from measurements on said fluid prior to circulating said fluid, carrying out complex dynamic viscosity measurements with a suitable detector arranged on a line through which said fluid circulates, so as to obtain a law of variation of the complex dynamic viscosity $\eta^*$ as a function of $2\pi f$, where f is the excitation frequency of the detector, deducing the rheogram of the fluid, i.e. a law of variation of the viscosity h as a function of the shear rate ($\dot\gamma$), from said calibration function and said complex viscosity measurements calculating at least one characteristic parameter of the rheology of the fluid from said rheogram, repeating these stages after a predetermined time interval, deducing from the evolution of said parameter the evolution of the characteristics of the fluid.

2. A method as claimed in claim 1, wherein said measurements on said fluid prior to circulating said fluid include measurements performed with said detector suited to obtain the complex dynamic viscosity and measurements performed with a FANN type rotating viscometer.

3. A method as claimed in claim 1, wherein a new calibration function is calculated upon each fluid change.

4. A method as claimed in claim 1, wherein apparent viscosity, plastic viscosity and yield value are calculated by means of said rheogram.

5. A method as claimed in claim 1, wherein said viscosity variation laws are modeled according to one of the models selected from the group consisting of Ostwald (power law), Hershell-bulkley, and Casson.

6. A system for monitoring the evolution of characteristics of a fluid circulating in a well for example, characterized in that it comprises:
- a detector arranged on a line through which said fluid circulates, suited to measure the complex dynamic viscosity,
- calculation means for implementing the method as claimed in claim 1,
- means for recording the evolution of the fluid characteristics.

* * * * *